United States Patent [19]
Efange et al.

[11] Patent Number: 5,789,420
[45] Date of Patent: Aug. 4, 1998

[54] AZAVESAMICOLS

[75] Inventors: Simon Mbua Ngale Efange, Plymouth, Minn.; Stanley M. Parsons, Santa Barbara, Calif.

[73] Assignee: Regents of the University of Minnesota, Minneapolis, Minn.

[21] Appl. No.: 122,159

[22] Filed: Sep. 17, 1993

Related U.S. Application Data

[62] Division of Ser. No. 893,129, Jun. 3, 1992, Pat. No. 5,338,852.

[51] Int. Cl.$^6$ .................. A01N 43/40; A61K 31/445; G01N 33/00
[52] U.S. Cl. .................. 514/316; 436/63; 436/96; 436/805
[58] Field of Search .................. 424/1.65, 1.85, 424/7.1, 9, 9.36, 9.6; 534/10, 14; 436/57, 63, 96, 805; 514/316

[56] References Cited

U.S. PATENT DOCUMENTS 5,077,035  12/1991  Wieland et al. .................. 424/1.1

OTHER PUBLICATIONS

Rogers et al., Synthesis, in Vitro Acetylcholine–Storage-–Blocking Activities, and Biological Properties of Derivatives and Analogues of trans–2–(4–Phenylpiperidino) Cyclohexanol (Vesauicol), *J. Med. Chem.* vol. 32, 1989, pp. 1217–1230.

*Primary Examiner*—John Kight
*Assistant Examiner*—Lara C. Kelley
*Attorney, Agent, or Firm*—Vidas, Arrett & Steinkraus

[57] ABSTRACT

The compounds are vesamicol (hydroxylated phencyclidine (PCP) isomer trans-2-(4-phenyl-piperidino)cyclohexanol) derivatives with anticholinergic properties termed herein "azavesamicols" in which the cyclohexyl group of vesamicol is replaced with a heterocycle of similar size, the piperidyl ring. The compounds bind to the vesamicol receptor, a cytoplasmically-oriented site on the cholinergic synaptic vesicle, which is associated with the vesicular transporter of acetylcholine.

2 Claims, 4 Drawing Sheets

AZAVESAMICOLS

This is a division of Ser. No. 07/893,129 filed Jun. 3, 1992, now U.S. Pat. No. 5,338,852.

BACKGROUND OF THE INVENTION

1. Field of the Invention

This invention relates to vesamicol derivatives that have anticholinergic properties.

2. Description of the Related Art

The vesamicol receptor, a cytoplasmically-oriented site on the cholinergic synaptic vesicle, is associated with the vesicular transporter of acetylcholine (reviewed by Marshall and Parsons entitled "The Vesicular Acetylcholine Transport System" in TINS, Vol. 10, No. 4, 1987). The location of this receptor provides opportunities for the investigation of presynaptic cholinergic phenomena associated with the release and/or storage of acetylcholine.

The prototypical vesamicol receptor ligand 2-(4-phenylpiperidinyl)cyclohexanol (1,vesamicol,AH5183) exhibits nanomolar affinity for this receptor (Bahr and Parsons, 1986). However, vesamicol also exhibits significant alpha-adrenoceptor activity (Estrella et al entitled "A further study of the neuromuscular effects of vesamicol (AH5183) and of its enantiomer specificity"., Br. J. Pharmacol, 93, 769–777 1988), an attribute which limits its usefulness in the study of presynaptic cholinergic function. In an earlier structure-activity study (Rogers et al., entitle "Synthesis in Vitro Acetylcholine-Storage Blocking Activities and Biological Properties of Derivative and Analogues . . . " in *Journal of Medicinal Chemistry*, Vol. 32, No. 6, 1989), the vesamicol analogs 2a, 2b and 3 were identified as potent ligands for this receptor. In addition to providing new insights into the topography of the vesamicol receptor, these novel analogs also represent lead structures for developing a new generation of potent and selective ligands for this receptor. Although 2b, a pseudo-irreversible ligand, has been used as a lead for developing a number of potentially useful ligands (Jung et al., "Radiotracer for Mapping Cholinergic Neurons of the Brain", in *Journal of Medicinal Chemistry*, Vol. 33, No. 8 1990; Kilbourn et al. entitled "Mouse Brain Distribution of a Carbon-11 Labeled Vesamicol Derivative: . . . " in *LifeSciences* 47:21 pp. 1155-1963 1990), the full implications accompanying the activity of 3 have yet to be realized.

In U.S. Pat. No. 4,522,965 which issued Nov. 12, 1985 to Stanley M. Parsons, a vesamicol derivative is described for use in blocking conduction at the neuromuscular junction in mammals. Parsons notes that it is desirable to produce a more effective compound than vesamicol for blocking presynaptic release of acetylcholine.

In an earlier study, Rogers et al. entitled "Synthesis in Vitro Acetylcholine-Storage Blocking Activities and Biological Properties of Derivative and Analogues . . . " in *Journal of Medicinal Chemistry*, Vol. 32, No. 6 (1989) noted that the vicinal aminoalcohol functionality was essential for vesamicol-like anticholinergic activity. Furthermore, these authors showed that benzo fused analogs like 2a and 2b were potent inhibitors of vesicular ACh transport. In contrast, those analogs which lacked a cyclohexyl moiety (e.g. 4a,4b) were found to exhibit substantially diminished activity.

In a subsequent study, we demonstrated that potent noncyclohexyl-containing vesamicol analogs could be obtained by attaching arylethyl substituents onto 4a. Case in point, compound 4c was found to be 59 times more potent than 4a.

Vesamicol has the ability to inhibit both the uptake of ACh into cholinergic synaptic vesicles and quantal release of this neurotransmitter from cholinergic neuron. Vesamicol binds reversibly to a unique cytoplasmically-oriented site, the vesamicol receptor, located on the cholinergic synaptic vesicle (and the prejunctional neuronal membrane) and thus interferes with the aforementioned processes. Given its location, the vesamicol receptor may be a useful presynaptic marker of cholinergic innervation. Such a receptor site would provide a suitable target for the development of radiotracers for mapping cholinergic pathways in vivo.

The study of cholinergic innervation in vivo is potentially of diagnostic value in neurodegenerative disorders such as Alzheimer's disease wherein significant decreases in cholinergic innervation have been detected early in the disease progression (Reisine et al entitled "Pre-and postsynaptic neurochemical alterations in Alzheimer's disease" in *Brain Research*, 159, 477–481 1978; Rossor et al entitled "A Post-Mortem Study of the Cholinergic and Gaba Systems in Senile Dementia" in *Brain* 105,313–330 1982; Bowen et al entitled "Biochemical Assessment of Serotonergic and Cholinergic Dysfuntion and Cerebral Atrophy in Alzherimers Disease" in *Journal of Neurchemistry* 1983; Mountjoy et al entitled "Correlation of Cortical Cholinergic and Gaba Deficits with Quantitatie Neurophathological Findings in Senile Demenita " in *Brain* (1984) 107, 507–518 1984). The potential utility of the vesamicol receptor as a presynaptic cholinergic marker has been demonstrated by preliminary characterization of [$^3$H]vesamicol binding in the rodent brain (Marien et al entitled "Quantitative autoradiography of brain binding sites for the vesicular acetylcholine transport blocker . . . " in *Proc. Nat'l Acad Sic.* USA 84 (1987), Altar et al entitled "[$^3$H] Vesamicol Binding in Brain . . . ", SYNAPSE 2:486–193 1988). In these studies, the distribution of radiolabelled vesamicol was found to correlate well with other markers of cholinergic innervation. In addition, a significant decrease in cortical [$^3$H]vesamicol binding was obtained by lesioning a known cholinergic pathway (Altar et al 1988; Marien et al 1987).

Alzheimer's disease (AD) is a progressive neurodegenerative disorder associated with loss of memory and other cognitive functions. Recent epidemiologic studies suggest that 10% of adults over the age of 65 (about 4 million people) may suffer from this disorder.

Progress in the diagnosis and subsequent clinical management of AD has been slowed by the absence of both a reliable diagnostic procedure and an established therapeutic regimen. Currently, a definitive diagnosis of AD can only be made by histopathologic examination of brain tissue. Brain biopsy is not practical in clinical practice. Therefore, patients are subjected to a battery of psychometric, radiologic and chemical tests designed to exclude the presence of other diseases. Only 50% of these diagnoses are found to be accurate at autopsy.

An important feature of AD is that neurons which produce the neurotransmitter acetylcholine (cholinergic neurons) progressively degenerate. More importantly, the extent of this degeneration correlates with the severity of AD. Biochemical markers of cholinergic innervation could be used as reliable indicators of AD. The anticholinergic vesamicol binds selectively to a unique site (the vesamicol receptor) on the cholinergic synaptic vesicle, and thus inhibits the uptake of acetylcholine into the synaptic vesicle.

Radiolabeled ligands for the vesamicol receptor will be clinically useful radiopharmaceuticals for evaluating cholinergic innervation in the living human brain. In conjunction with SPECT, these radioligands which bind selectively to the vesamicol receptor should identify the cholinergic deficit in the Alzheimer's brain.

The art described in this section is not intended to constitute an admission that any patent, publication or other information referred to herein is "prior art" with respect to this invention, unless specifically designated as such. In addition, this section should not be construed to mean that a search has been made or that no other pertinent information as defined in 37 C.F.R. § 1.56(a) exists.

SUMMARY OF THE INVENTION

The present invention describes the synthesis and vesicular storage-inhibitory properties of a series of compounds derived from the novel vesamicol analogs 5(5-azavesamicol) and 6(4-azavesamicol).

Although 2a, 2b and 3 emerged as potent VR ligands, subsequent development of potent radiolabeled and/or fluorescent probes for this receptor has relied almost exclusively on the easily functionalized analogue b. However, the potency of 3, a nonfused 4-substituted vesamicol analogue suggested to us that the development of novel high-affinity vesamicol receptor ligands could be accomplished without extensive modification of the parent vesamicol nucleus.

The addition of a small lipophilic group to 4a to yield 4b also resulted in a 30-fold increase in activity. This observation suggested to us that further increases in potency could be achieved, even in the absence of the cyclohexyl moiety, by increasing the size of the substituent on the hydroxyl-containing carbon atom.

We postulated that a new generation of potent conformationally restrained vesamicol-like anticholinergics could be developed by substituting the cyclohexyl group with a heterocycle of similar size,the piperidyl ring. Since the nitrogen atom of this ring can be easily functionalized, the new parent structure would be a useful intermediate for developing anticholinergic drugs and fluorescent or radiolabeled probes for studying presynaptic cholinergic function. Finally, the nitrogen of this new piperidine ring could be introduced at various orientations relative to the aminoalcohol functionality to optimize biological activity. To test this hypothesis, we proposed the novel compounds 5 (3-azavesamicol) and 6 (4-azavesamicol). In the regioisomers 5 and 6, the new ring nitrogen and the hydroxyl group are located 1,3 and 1,4 respectively. For simplicity, the compounds 5 and 6 have been named Trozamicol and Prezamicol, respectively.

These compounds may be radiolabeled and used as reliable targets for radiotracer development. Additionally, since the compounds of the invention are anticholinergics, they may be used where anticholinergics are desired, such as in pesticides or muscle relaxants. The radiolabel may be a transition metal or any acceptable tag which will make the compound detectable outside the brain.

BRIEF DESCRIPTION OF THE DRAWINGS

A detailed description of the invention is hereafter described with specific reference being made to the drawings in which.

DESCRIPTION OF THE PREFERRED EMBODIMENTS

Chemistry

Figure 4:
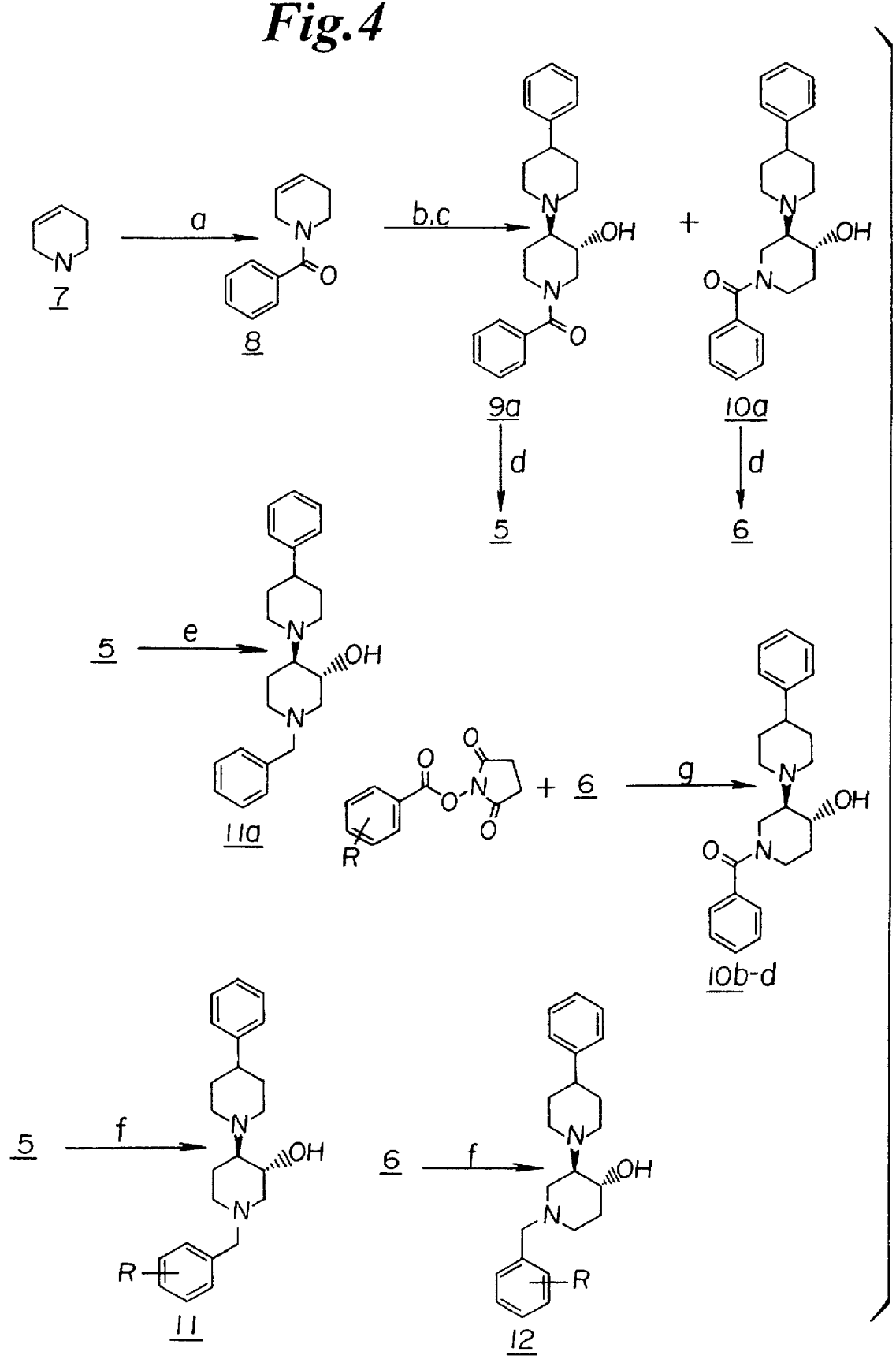
FIG. 4 shows synthesis of Azavesamicols a: Benzoyl chloride, Et$_3$N; b:m-CPBA, CH$_2$Cl$_2$; c: 4-phenylpiperidine, EtOH, heat; d: 6N HCl, reflux; e: LiAlH$_4$, THF, reflux; f: substituted benzyl chloride, NaHCO$_3$, aq. EtOH, reflux; g: CH$_3$CN, reflux, the various R groups may include H, F, Br, I, CH$_3$.

The key intermediates 9a and 10a were obtained in a 1:1 ratio from 7 in 50% combined yield as outlined in FIG. 4. The regioisomers were easily separated by HPLC, and the less mobile regioisomers was determined by x-ray crystallography to be 10a. The racemate (dl)–10a was resolved chromatographically to yield (+)–10a and (−)–10a, respectively. The enantiomeric purity was determined by HPLC on a Chiralcel OD column. X-ray crystallographic analysis also revealed that the absolute configuration of (+)–10a is 1S,2S. This configuration is identical to that identified for (+)-vesamicol in a previous study (Rogers et al., entitled "Synthesis in Vitro Acetylcholine-Storage Blocking Activities and Biological Properties of Derivative and Analogues . . . " in *Journal of Medicinal Chemistry*, Vol. 32, No. 6 1989). Acid-catalyzed hydrolysis of 9a and 10a yielded 5 (86%) and 6 (86%), respectively. These two intermediates were subsequently derivatized to yield the target compounds in respectable yields. The physical characteristics and yields of target compounds are provided in Table 1.

Results and Discussion
Structure-Activity Relationships

As evident in the in vitro binding data (Table 2), replacement of the cyclohexyl moiety with a suitably substituted heterocycle produces potent vesamicol analogs. However, the potency is influenced by a number of factors. While the benzoyl analog 9a is essentially in inactive, the corresponding regioisomers 10a is almost as potent as vesamicol. This observation clearly suggests that the preferred orientation of the nitrogen of the new piperidine ring relative to the hydroxyl group is 1,4 (referred to as the 1,4 series). Reduction of 9a to the benzyl analog 11a increases the potency by 15 to 20 times. Since the benzyl group is less constrained than the benzoyl group, the increase in potency may be related to flexibility. Alternatively, the basicity of the nitrogen may contribute to increased affinity. Substitution with bromine at the ortho position of 11a results in a slight but noticeable increase in activity (compare 11a vs 11b). In the 1,4 series reduction of 10a to 12a also results in increased potency. However, the increase is less pronounced than in the 1,3 series. The introduction of a small electron withdrawing group into the benzyl group of 12a also enhances potency (compare 12a vs. 12d). Increasing the size of the electron withdrawing substituent did not significantly alter the potency (compare 12d vs. 12g). Finally, the biological activity was not sensitive to the location of the substituent on the ring (compare 12e vs 12f or 12g). These observations suggest that lipophilic electron withdrawing substituents are preferred in this region of the vesamicol receptor. The potency of these new compounds also supports our hypothesis that the cyclohexyl group may be replaced with heterocycles. It is also worth noting that compounds in the entitled "Acyclic Analogues of 2-(4-phenylpiperidino)cyclohexanol (Vesamicol): . . . " in *J. Med. Chem.* 34:8 2638–2643 1,4-series are more potent than our acyclic compounds described earlier (Efange et al., 1991). A superposition of 4c, one of these compounds, and 12a suggests that the latter can reach further into a given receptor site. In addition, 12a and 4c can explore different regions of the receptor given their flexibility. These structural differences, including the presence of a basic nitrogen in 12a, may underlie the enhancements in potency observed.

Pharmacological Studies in Mice in vivo anticholinergic activity was evaluated in mice. Blockade of cholinergic neurotransmission (or anticholinergic activity) was manifested in a rapidly developing respiratory distress, spasms and paralysis. At lethal doses these symptoms were followed by death within 10 min. As evident in Table 3, several of the compounds tested were lethal at doses as low as 5 and 10 umol/Kg. The pure enantiomer (+)-10a elicited anticholinergic effects even at 2.5 umol/Kg. All of the potent compounds belong to the 1,4 series, an observation consistent with the in vitro data discussed above. These data clearly demonstrate that the anticholinergic activity observed in vitro can be manifested in vivo.

Tissue Distribution Studies

The tissue distribution of radiolabeled 12h was studied in male Wistar rats. Following intravenous administration of radioiodinated (+)-12h in the rat, high levels of radioactivity were found in the lung and kidney after 5 min (see Table 4). Moderate to low levels were found in the liver, heart, thyroid and spleen. At 5 min post-injection, the level of radioactivity in the brain was 1.06% of the injected dose. This level decreased to 0.51% after 60 min and further decreased to 0.39% after 3 hrs. Levels in the thyroid were moderate at the beginning but increased significantly by 3 hrs post-injection. In contrast to (+)-[$^{125}$I]-12h, the levorotatory antipode showed a higher accumulation and longer retention in the brain. At 5 min post-injection 1.67% of the injected dose was found in the brain. This level remained essentially unchanged throughout the duration of the study (see Table 5). Based on these studies, the levorotatory isomer shows higher accumulation and a longer retention in the brain.

Autoradiographic Studies

Figure 1A:
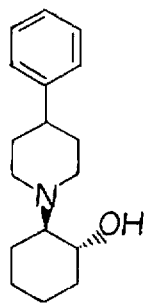
FIG. 1 shows the absolute stereochemistry of (+)-10 and (-)-vesamicol.
Figure 1B:
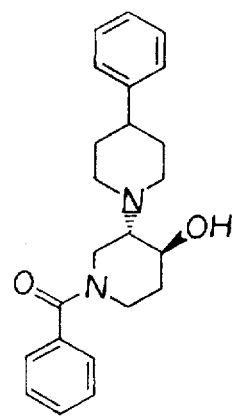
Figure 5:
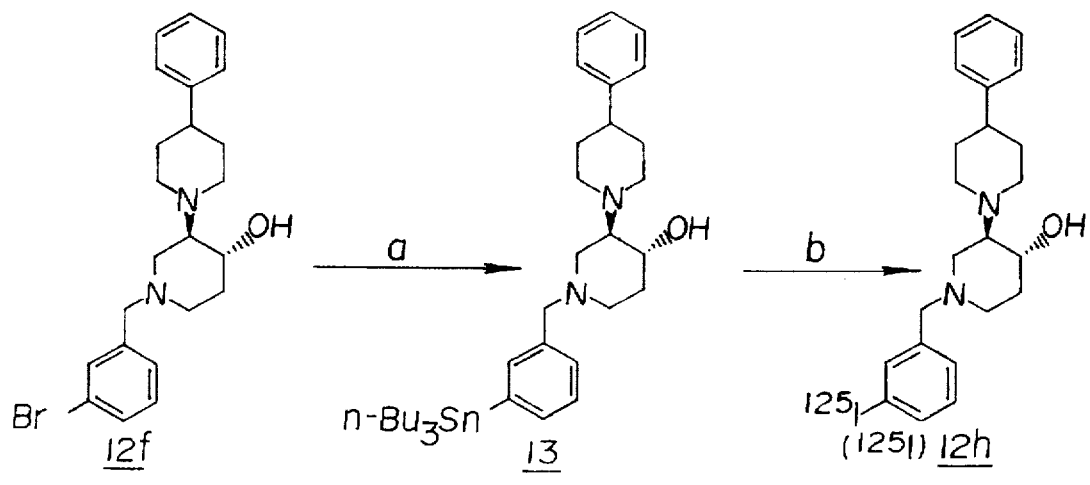
FIG. 5 shows the radiolabelling sequence a: n-BuLi, -78° C., n-BU$_3$SnCl; b: Na$^{25}$I, Chloramine T, HOAc.
Figure 2:
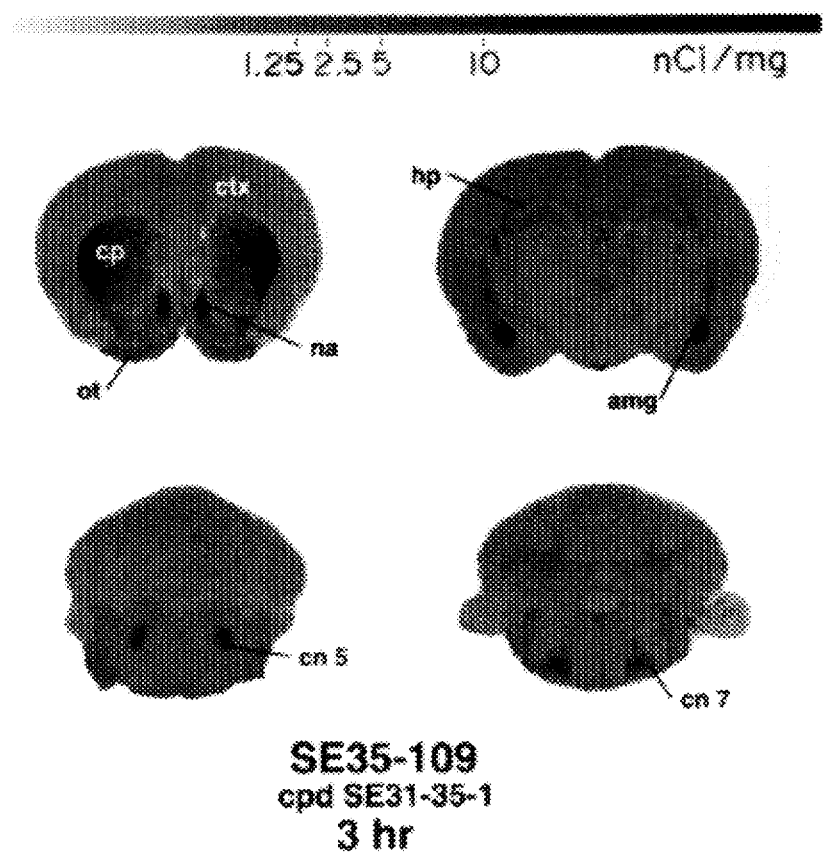
FIG. 2 shows regional distribution of (+)-[$^{125}$I]12h in the rat brain as revealed by ex vivo autoradiography.
Figure 3:
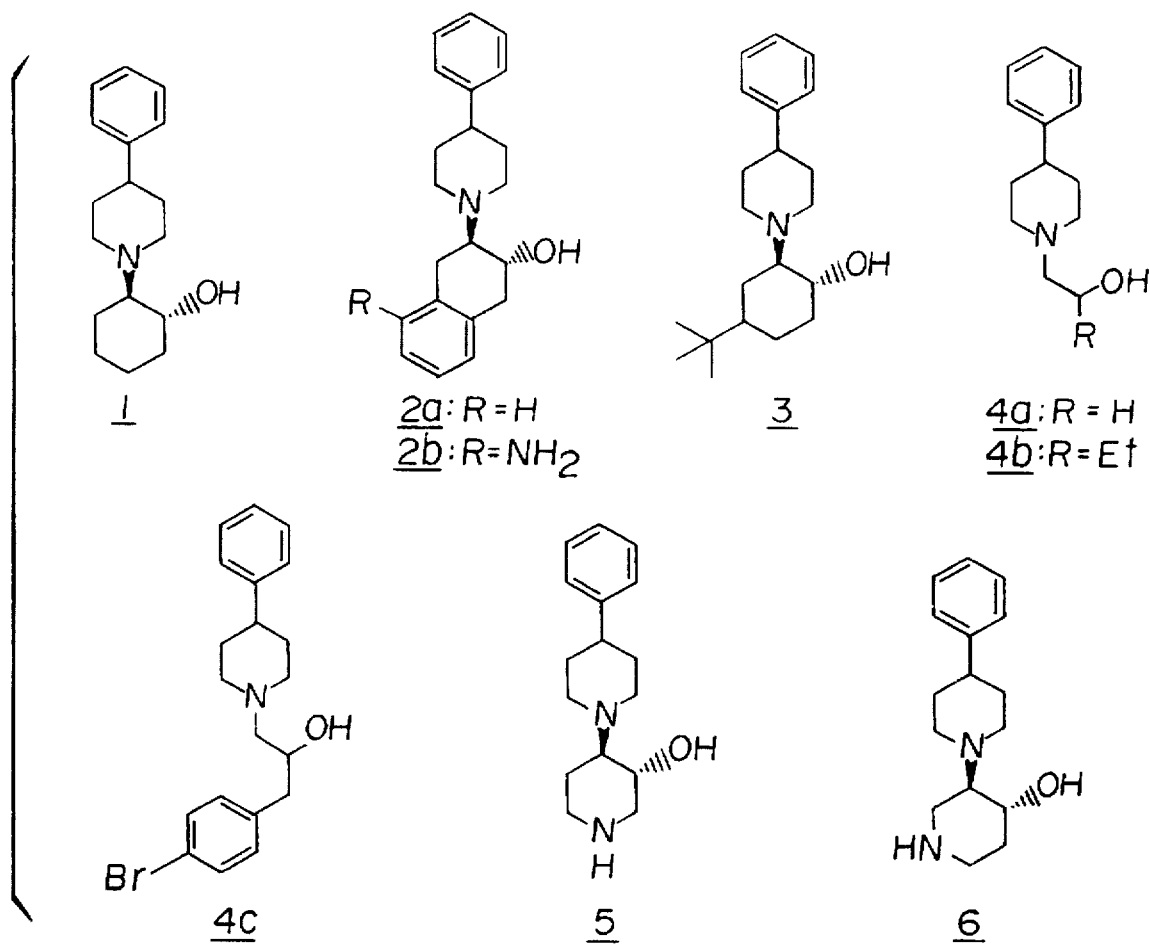
FIG. 3 shows Vesamicol analogs.

As revealed by ex vivo autoradiography (see FIG. 2), the regional distribution of (+)-[$^{125}$I]12h in the rat brain shows high levels of radioactivity in the interpeduncular nucleus (ip), olfactory tubercle (ot), nucleus accumbens (na), amygdala (amg), caudate-putamen (cp) and the nuclei of the fifth and seventh cranial nerves (cn5 and cn7). Moderate levels of activity were observed over the cortex (ctx), hippocampus (hp) and cerebellum. This pattern of activity is consistent with known patterns of cholinergic innervation in the mammalian brain. In contrast, the distribution of (−)-[$^{125}$I]-12h reveals high levels of radioactivity over the cortex, caudate- putamen, hippocampus and red nucleus. In addition, the levels in the cortex appeared to be slightly higher than those observed in the caudate-putamen. That the distribution of (−)-[$^{125}$I]-12h contrasts with that of the corresponding antipode (+)-[$^{125}$I]-12h is consistent with the poor in vitro activity of the levorotary enantiomers of this series. This study therefore confirms that even at the tracer level, the dextrorotary antipodes are sufficiently potent to selectively bind to the vesamicol receptor, a presynaptic cholinergic site.

Conclusions

By replacing the cyclohexyl group of vesamicol with the piperidyl group we have produced a new series of potent inhibitors of vesicular acetylcholine transport. The favored orientation of the new ring nitrogen relative to the hydroxyl group is 1,4 . The in vitro anticholinergic activity of these compounds is matched by potent pharmacological activity in mice. Furthermore, these compounds are sufficiently potent to retain selectivity for cholinergic targets even at the tracer level.

In addition to resolving the question of regiochemistry, X-ray crystallographic studies also revealed the absolute configuration. In contrast to the vesamicol series, the absolute configuration of the active enantiomers in the azavesamicol series is 1S,2S. The difference in absolute configuration between the two series suggests that the two series (represented by (−)-vesamicol and (+)-10a may bind to the vesamicol in dissimilar modes. In addition, this discrepancy is particularly significant in that it distinguishes the azavesamicols as a separate subclass of amino alcohol-containing anticholinergics.

Based on the ease of functionalization of Trozamicol, 5, fluorescent sidechains can be easily introduced to produce fluorescent probes for cholinergic system. Other sidechains containing radionuclides may be attached to 6 to produce novel radiotracers for mapping the cholinergic system. Suitably substituted sidechains (such as perfluorinated aromatics) may yield NMR contrast agents. Finally, these new agents may be used for therapeutic applications which require a down regulation of cholinergic function.

Prezamicol and Trozamicol are easily modified to add sidechains from the Nitrogen atom. The sidechains may be azidoaryl, azidoarylalkyl, azidoheteroaryl or azidoheteroaroyl; a chelating sidechain complexed with a radionuclide which emits gamma or positron radiation; a sidechain containing a fluorescent or visible dye or chromophore; capable of tissue penetration and subsequent external detection by a photoscanning device; or a chelating sidechain complexed with a paramagnetic cation capable of enhancing contrast in magnetic resonance imaging.

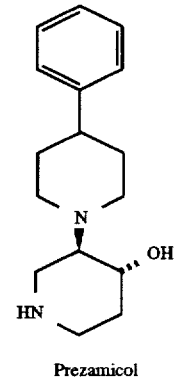

Prezamicol

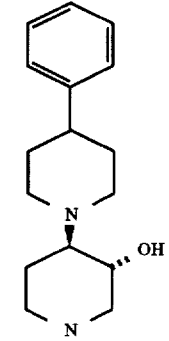

Trozamicol

These compounds are useful for many applications. They may be used in a method for noninvasively mapping cholinergic innervation in a living brain, which comprises injecting a subject with an effective amount of a radiolabeled compound based on an azavesamicol with a chelating sidechain complexed with a radionuclide such as Tc-99m, Re-18b and Ga-68 which emits gamma or positron radiation capable of tissue penetration and subsequent external detection by a photoscanning device; and subsequently scanning with said photoscanning device to visualize cholinergic innervation.

The azavesamicols may be used in a method for photoaffinity labelling of the vesamicol protein, which comprises treatment of tissues with an effective amount of photoaffinity label including azavesamicol wherein the sidechain is azidoaryl, azidoarylalkyl, azidoaroyl, azidoheteroaryl or azidoheteroaroyl; and inducing chemical bond formation between the azido group and the vesamicol receptor by exposure to light.

The azavesamicols may be used in a method for visualization of cholinergic innervation in the mammalian brain which comprises the application of an effective amount of aa azavesamicol including a sidechain containing a fluorescent or visible dye or chromophore; and subsequent visualization of the tissue with light.

The azavesamicols may be used in a method for blocking cholinergic neurotransmission in mammals which involves the application of an azavesamicol composition as an active ingredient including a sidechain that is alkyl, arylalkyl, cycloalkyl, heteroalkyl or acyl.

The azavesamicols may be used in a method for noninvasive detection of cholinergic innervation in a living brain, which comprises injecting a subject with an effective amount of a magnetic resonance contrast agent comprising an azavesamicol with a chelating sidechain complexed with a paramagnetic cation capable of enhancing contrast in magnetic resonance imaging; and subsequently scanning with a magnetic resonance imager.

The azavesamicols may be used in a method for autoradiographic visualization of the distribution of cholinergic pathways in animal tissue which comprises introduction by injection to a subject or incubation of a tissue sample with a radiolabelled azavesamicol with a sidechain containing a radiolabel; and subsequent visualization by autoradiography.

Experiential Section
General Section:

Synthetic intermediates were purchased from Aldrich, Inc. (Milwaukee, Wis.) and were used as received. Solvents were distilled immediately prior to use. Commercially available reagents were used without subsequent purification. Tissue Tek OCT compound was purchased from Miles Inc., Elkhart, Ind. Rats and mice were obtained from Sasco Inc., Omaha, Nebr.

All air-sensitive reactions were carried out under nitrogen. Standard handling techniques for air-sensitive materials were employed throughout this study. Melting points were determined on a Mel-Temp melting point apparatus and are uncorrected. The specific rotation was determined on an automatic polarimeter (Autopol III, Rudolph Research, Flanders, N.J.). $^1$H NMR spectra were recorded on an IBM-Brucker spectrometer at 200 MHz. NMR spectra are references to the deuterium lock frequency of the spectrometer. Under these conditions, the chemical shifts (in ppm) of residual solvent in the $^1$H NMR spectra were found to be respectively; $CHCl_3$, 7.26; DMSO, 2.56; HOD, 4.81. The following abbreviations are used to describe peak patterns when appropriate: br=broad, s=singlet, d=doublet, t=triplet, q=quartet, m=multiplet. Both low- and high-resolution MS were performed on an AEI MS-30 instrument. Elemental analyses were performed by Atlantic Microlab, Inc., Norcross, Ga. Unless otherwise indicated, these values are within ±0.4% of the theoretical.

Column chromatography was performed using "Baker Analyzed" silica gel (60-200 mesh). Preparative chromatography was performed on either a Harrison Research Chromatotron using Merck 60 $PF_{254}$ silica gel or a preparative HPLC (Rainin Instrument Co.) using a 41.1 mm ID Dynamax silica gel column (at a solvent delivery rate of 80 ml/min.). Enantiomeric purity was determined by HPLC with a Chiralcel OD column (isopropyl alcohol: hexane: $Et_3N$, 10:89:1; flow rate 1 ml/min.). Analytical TLC was performed on Analtech glass TLC plates coated with silica gel GHLF and were visualized with UV light and/or methanolic iodine. All target compounds were checked for purity by HPLC (silica gel, 10–20% isopropyl alcohol- hexanes, trace $Et_3N$). Representative procedures for the steps shown on Scheme 1 are provided below as Procedures A–G.

Procedure A

1-Benzoyl-3-hydroxy-4-(4-phenylpiperidinyl)piperidine (9a) and 1-Benzoyl-4-hydroxy-3-(4-phenylpiperidinyl)piperidine (10a)

Benzoyl chloride (6.22, 44.3 mmol) was added dropwise to a cold (icebath) stirring solution containing 3.2 g (38.5 mmol) of 1,2,3,6-tetrahydropyridine in $Et_3N$ (30 ml). Following the addition, the mixture was allowed to slowly warm up to room temperature. After 24 hours, the reaction mixture was diluted with $H_2O$ (30 ml) and extracted with $CH_2Cl_2$ (85 ml). The organic extract was washed with saturated $NaHCO_3$ (50 ml), dried over anhydrous $Na_2SO_4$ and concentrated in vacuo to yield a chromatographically homogeneous yellow liquid (quant); $^1$H NMR ($CDCl_3$) δ 2.20 (d,2H), 3.46 (br s, 2H), 3.86 (br s, 2H), 4.20 (br s, 1H), 5.86 (m, 1H), 7.40 (s, 5H. The latter was redissolved in $CH_2Cl_2$ (140 ml) and cooled in an icebath. To this cold stirring solution m-CPBA (14.40 g; 50–60% pure) was added portionwise over 10 min. After completion of the addition, the reaction mixture was maintained a 4° C. for 1 hour and allowed to slowly warm up to room temperature. Sixteen hours later, the reaction mixture was diluted with $CCl_4$ (100 ml) and filtered to remove precipitated 3-chlorobenzoic acid. The filtrate was washed consecutively with 5% aq. $NaHSO_3$ (2×100 ml) and satd $NaHCO_3$ (2×100 ml), dried over anhydrous $Na_2SO_4$ and concentrated in vacuo to provide 6.93 g of the crude epoxide as a brown syrup. A solution of the epoxide and 5.64 g (35.0 mmol) of 4-phenylpiperidine in EtOH (100 ml) was refluxed for 15 hours, cooled and concentrated to a brown residue, the latter was dissolved in $CH_2Cl_2$ (150 ml) and the resulting solution was washed with $H_2O$ (70 ml), dried over anhydrous $Na_2SO_4$ and concentrated to a syrup which was purified by preparative HPLC (silica gel; i-PrOH 910): hexanes (90): $Et_3N$(1) to yield two major components. The more mobile component identified as 9a was obtained in 25% yield: The corresponding hydrochloride was recrystallized from i-PrOH-MeOH mp 220°–223° C.; $^1$H NMR ($CDCL_3$) δ 1.61–1.89 (m,6H), 2.29 (t,1H), 1.46–1.53 (m,2H), 2.81 (m,4H), 2.96 (m,1H), 3.45 (m,1H), 3.83 (m, 1H), 4.69 (m,1H), 4.88 (m,1H), 7.19–7.40 (m,10H). The less mobile component was assigned the structure 10a: mp (HCl) 248°–251° C.; $^1$H NMR ($CDCl_3$)δ 1.50–3.07 (m,12H), 3.67–3.79 (m,4H), 4.78 (m,1H), 4.92 (m,1H), 7.20–7.44 (m,10H). The less mobile component was assigned the structure 10a: mp (HCl) 248°–251° C.; $^1$H NMR.

Procedure B

3-Hydroxy-4-(4-phenylpiperidinyl)piperidine (5)

A suspension of 2.0 g (5.5 mmol) of 8 in 6N HCl (50 ml) was refluxed overnight. The reaction was shown to be complete by TLC (silica gel; 50% acetone - hexanes) after 24 hours. The reaction mixture was cooled and filtered to remove precipitated benzoic acid. The filtrate was extracted with $CH_2Cl_2$ (50 ml) and concentrated to a solid residue. The latter was redissolved in MeOH (25 ml), concentrated to a minimum volume and triturated with i-PrOH to yield, after filtration, 1.57 g (86%) of a white solid: mp 279°–282° C.; $^1H$ NMR $D_2O$) δ 1.95–2.15 (m,5H), 2.46 (d,1H, J=12Hz), 2.88–3.02 (m,2H), 3.06–3.16 (t,1H, J=14Hz, J=3Hz), 3.30–3.39 (t,1H, J=12Hz, J=2.4Hz), 3.42–3.66 (m,7H), 4.19–4.28 (m,1H), 7.26–7.40 (m,5H). A similar procedure yielded 1.6 g (86%) of 6: mp 205–206° C.; $^1H$ NMR ($D_2O$) 1.75–1.92 (m,1H), 1.95–2.20 (m,4H), 2.34 (d,1H), 2.91 (brs,1H), 3.08 (t,1H), 3.30–3.62 (m,6H), 3.71 (d,1H), 3.92 (d,1H), 4.22 (m,1H), 7.24–7.39 (m,5H).

Procedure C
1-Benzyl-3-hydroxy-4-(4-phenylpiperidinyl)piperidine (11a)

A solution of 1.08 g (2.96 mmol) of 8 in dry THF (20 ml) was added dropwise under $N_2$ to a stirring suspension of LiAlH$_4$ (0.5 g, 13.2 mmol) in anhydrous THF (25 ml). Following the addition, the reaction mixture was refluxed overnight. After 22 hours, the mixture was cooled to room temperature and diluted with dry THF (30 ml). The reaction was quenched by sequential dropwise addition of $H_2O$ (0.5 ml), 15% NaOH (0.5 ml) and $H_2O$ (1.5 ml). The resulting mixture was filtered, and the cake was washed repeatedly with THF and discarded. The filtrate was dried over anhydrous $Na_2SO_4$ and concentrated to a chromatographically homogeneous pale yellow syrup which solidified on standing. The solid was redissolved in MeOH (15 ml). The solution was cooled in an icebath and HCl(g) was bubbled through the solution for 5 minutes with concomitant precipitation of the hydrochloride. The latter was collected by filtration washed consecutively with a minimum volume of MeOH and cold i-ProH, and dried in vacuo yield 0.89 g (71%) of a white solid: mp 288°–290° C.; $^1H$ NMR (DMSO-$d_6$+$D_2O$)δ 1.87–2.02 (m,5H), 2.70 (d,1H), 2.77 (m,1H), 2.90 (t,1H), 3.04 (t,1H), 3.20–3.45 (m,7H), 4.11 (m,1H), 7.16–7.28 (m,5H), 7.39–7.46 (m,5H).

Procedure D
1-(4-Bromobenzyl)-4-hydroxy-3-(4-phenylpiperidinyl) piperidine (12g)

A mixture of 0.5 g (1.5 mmol) of the hydrochloride of 4, 0.41 g (1.66 mmol) of 4- bromobenzyl bromide and 0.51 g (6.0 mmol) of NaHCO$_3$ in EtOH (13 ml) and $H_2O$ (6 ml) was heated under reflux for 24 hr. The mixture was cooled to room temperature and extracted with $CH_2Cl_2$ (3×20 ml). The combined organic extracts were dried over $Na_2SO_4$ and concentrated in vacuo to a brown syrup. The latter was redissolved in $CH_2Cl_2$ and passed through a short column of silica gel (eluted with $CH_2Cl_2$, 99: Et$_3$N, 1). The eluent was concentrated to provide 0.58 g of a golden brown syrup which was dissolved in MeOH and converted to the corresponding hydrochloride as described above. The hydrochloride was crystallized from cold MeOH, and collected by filtration to provide 0.45 g (60%) of a white powder: mp 159°–161° C.; $^1H$ NMR (CDCl$_3$) δ 1.57–2.20 (m,9H), 2.25 (t,1H), 2.52 (m,2H), 2.72 (m,1H), 2.82 (br s,2H) 3.04 (m,2H), 3.52 (m,2H), 3.73 (s,1H), 7.17–7.33 (m,7H), 7.48 (m,2H).

Procedure E
4-Hydroxy-1-(2-iodobenzoyl)-3-(4-phenylpiperidinyl) piperidine (10b)

Dicyclohexylcarbodiimide (2.48 g, 12 mmol) was added to a solution of 2-iodobenzoic acid (2.48 g, 10.0 mmol), and N-hydroxysuccinimide (1.26 g, 11 mmol) in $CH_2Cl_2$ (75 ml). The reaction mixture was stirred for 20 hrs and filtered to remove precipitated dicyclohexylurea. The filtrate was concentrated in vacuo to minimum volume and filtrated with hexanes. The resulting precipitate was collected by filtration, washed with hexanes and dried to yield the activated ester as a white powder (3 g, 90%); $^1H$ NMR (CDCl$_3$) ε2.84 (s, 4H), 7.21 (br s, 1H), 7.42 (s, 1H), 8.02 (br s, 2H). This material was used without purification. A suspension of the amino alcohol dihydrochloride 5 (0.33 g; 1.0 mmol) and the activated ester (0.34 g; 1.0 mmol) in reagent grade acetonitrile (20 ml) and Et$_3$N (6 ml) was refluxed for 21 hours, cooled to room temperature and concentrated in vacuo. The residue was treated with $H_2O$(30 ml) and extracted with $CH_2Cl_2$ (3 ×30 ml). The combined organic extracts were dried over anhydrous $Na_2SO_4$, and concentrated to a brown residue which was purified by radial flow chromatography (silica gel: acetone (30%): hexanes (70): Et$_3$N(1)). The desired fractions were concentrated to yield a pale yellow foam which was converted to the hydrochloride in methanol. The product crystallized from cold methanol to yield 0.32 (61%) of a white solid: mp 263°–264° C.

Procedure F
4-Hydroxy-1-(4-nitrophenyl)-3-(4-phenylpiperidinyl) piperidine (12l)

A solution of 0.50 g (1.50 mmol) of the hydrochloride of 5 and 0.17 g (3.16 mmol) of NaOMe in MeOH (20 ml) was stirred for 5 min and concentrated in vacuo. The resulting solid was dried in vacuo at 50° C., and redissolved in dry DMF (10 ml). Sodium carbonate (0.10 g; 0.9 mmol), and p-fluoronitrobenzene (0.42 g, 3.0 mmol) were then added, and the resulting solution was refluxed under nitrogen. After 15 hours, heating was stopped. The reaction mixture was cooled and concentrated in vacuo. The residue was triturated with $CH_2Cl_2$ (30 ml) and filtered to remove insoluble material. The filtrate was concentrated in vacuo and purified by radial flow chromatography (silica gel, 35% $CH_2Cl_2$— hexanes). The desired fractions were concentrated to a residue which was triturated with Et$_2$O—hexane, filtered and dried to yield 0.28 g (49%) of the fluffy yellow solid: mp 163°–164° C.; $^1H$ NMR (CDCl$_3$) 51.69–4.08 (m,18H), 7.02 (2,2H), 7.28 (m, 5H), 8.05 (d, 2H, J=10Hz); CIMS (NH$_3$) m/e (intensity) 381 (M$^+$, 39.64).

The free base was converted to the corresponding hydrochloride as described above and subsequently recrystallized from i-PrOH: mp 247°–250° C.; $^1H$ NMR (CDCl$_3$) δ 1.66 (m,2H), 1.80–2.00 (m,3H), 2.19–2.24 (d,1H, J=12 Hz), 2.35–2.65 (m,3H), 2.88(m,4H), 3.14 (d,1H), 3.68–3.85 (m,2H), 3.97 (d,1H), 4.09 (d,1H, J=18Hz), 6.83 (d,2H), 7.24 (d,3H), 7.33 (m,2H), 8.12 (d,2H).

Procedure G
1-(3-Tri-n-butylstannylbenzyl)-4-hydroxy-3-(4-phenylpiperidinyl)piperidine(13)

A solution of n-BuLi (4.0 mmol) in hexanes (1.6 ml) was added dropwise under $N_2$ to a stirring solution of 12g (0.77 g; 1.8 mmol) in dry THF (10 ml) cooled to −70° C. (Dry Ice-acetone). After stirring at −70° C. for 135 min, a solution of n-Bu$_3$SnCl (0.65 g; 2.0 mmol) in dry THF (8 ml) was added over 10 min. The Dry Ice-acetone bath was removed and the mixture was allowed to warm up to room temperature. After 20 hr, the reaction was quenched with 5% aq. NH$_4$Cl (25 ml) and extracted with $CH_2Cl_2$ (3×25 ml). The combined organics were dried over anhydrous $Na_2SO_4$ and concentrated to an oil. The crude product was purified by radial flow chromatography (silica gel; acetone (25): hexanes (75): Et$_3$N(1)) to yield 0.31 g (27%) of a pale yellow syrup: $^1H$ NMR (CDCl$_3$) δ1.59–2.07 (m,38H), 2.27 (t,1H), 2.48–2.60 (m,2H), 2.76 (t,1H), 2.94 (d,2H), 3.05 (d,2H), 3.44–3.61 (m,1H), 7.20–7.34 (m,9H).

Radio-labelling (+)- and (−)-4-hydroxy-1-(3-[I$^{125}$]iodobenzyl)-3-(4-phenyl-piperidinyl)piperidine 5 uL of a stock solution of 12f (13.4 mM in EtOH) was added to a 10×75 m borosilicate tube. To this solution was added EtOH (50 uL), HOAc (50 uL), a solution of 970 uCi of Na$^{125}$I in NaOH (pH 10) and Chloramine T (5 mg). The vial was capped with a rubber septum, vented with a charcoal filtered, vortexed for 15 sec and allowed to stand. After 15 min. the reaction was quenched with 5% aq. NaHSO$_3$ (100 uL). The reaction mixture was neutralized with satd. Na$_2$CO$_3$ (300 uL) and extracted with CH$_2$Cl$_2$ (3×0.5 ml). The combined organic extracts were dried over anhydrous Na$_2$SO$_4$, diluted with a solution of 40% oxalic acid in EtOH (50 uL) and concentrated under a stream of N$_2$. The residue which contained 730 uCi was redissolved in 50% i-PrOH-Hexane (100 uL) and purified by HPLC on a Chiralcel OD column (i-PrOH, 10: hexane, 89: Et$_3$N,1; flow rate 1ml/min) to provide 238 uCi (24% radiochemical yield) of (+)-|$^{125}$I|12h and 178 uCi (18.4% radiochemical yield) of (−)-|$^{125}$I|12h. The radiochemical purity of (+)-|$^{125}$I|12h and (−)-|$^{125}$I|12h was 95.7% and 98.8% respectively. Under the conditions used for chromatography, the retention times of the dextrotatory and levorotatory enantiomers were found to be 8.5 and 12.7 min. respectively. Their respective enantiomeric purities were greater than 98%.

Biological

Tissue Distribution Experiments

Four groups of male Wistar rats (n=4) weighing 200-350 g were used in these experiments. Each animal received, while under ether anesthesia, an intravenous injection of the radiotracer (3-5 uCi) dissolved in 0.1 mL of 50% aqueous ethanol. At 5, 30, 60 and 180 min post-injection, blood was collected from the anesthetized animal by cardiac puncture, and the animal was immediately sacrificed by cardiectomy. The organs and tissues of interest were harvested, transferred to preweighed tubes and counted in a Beckman gamma counter. The tubes were subsequently reweighed to give the weight of the corresponding tissues. Preweighed tubes containing 1 mL samples of a 1:100 dilution of the injected dose were also counted and used as reference for calculating the tissue accumulation of radioactivity. The accumulation of radiotracer was expressed as a percentage of injected dose per gram of tissue.

Blocking Experiments:

Two separate experiments each utilizing two groups of male Wistar rats (n=3) were performed.

Experiment 1. Animals in Group 1 (control) each received an intravenous injection of the radiotracer (4.7 uCi in 100 uL of 50% aq. EtOH). Animals in Group 2 were injected intravenously with a similar dose of the radiotracer mixed with (dl)-vesamicol (1.5 umol/Kg). At 60 min post-injection, the animals were sacrificed and the tissues were harvested as outlined above.

Experiment 2. Animals in Group 1 were injected intravenously at t=0 with 100 uL of 50% aq. EtOH (vehicle). The animals in Group 2 received, at the same time, intravenous injections of (dl)-vesamicol (1.01 umol/Kg) in 58% aq. EtOH. After 15 min. animals in both groups were injected intravenously with the radiotracer (2.0 uCi in 100 uL of 50% aq. EtOH). All animals were sacrificed after a total elapsed time of 45 min. Tissues were harvested as described above.

Ex-vivo Autoradiographic Studies

Two groups of male Wistar rats (n=2) were used in these experiments. Each animal in the first group received an i.v. injection of (+)-[$^{125}$I]12h (385 uCi in 0.1/ml of 50% aq. EtOH). Similarly, animals in the second group received 330 uCi of (−)-[$^{125}$I]12h (in 0.1 ml of 50% aq. EtOH). After 3 hrs, the animals were sacrificed by decapitation. The brains were carefully removed, embedded in Tissue Tek OCT medium and frozen to 37° C. Twenty micron thick coronal brain slices were subsequently obtained by sectioning rostrocaudally with a Reichert HistoSTAT microtome at −15°. The tissue sections were apposed to Kodak NMC film accompanied by $^{125}$I-labeled external standards ($^{125}$I-Microscales from Amersham). For delineation of cytoarchitecture, adjacent tissue sections were subjected to Nissl staining.

TABLE 1

Characteristics of azavesamicols

| Compound | R | Formula[a] | Method | M.P. (°C.) |
|---|---|---|---|---|
| 5 | — | C$_{16}$H$_{24}$N$_2$O.2HCl.¾H$_2$O | B | 279-282 |
| 6 | — | C$_{16}$H$_{24}$N$_2$O.2HCl.¾H$_2$O | B | 205-206 |
| 9 a | H | C$_{23}$H$_{28}$N$_2$O$_2$.HCl.½H$_2$O | A | 220-223 |
| 10 a | H | C$_{23}$H$_{28}$N$_2$O$_2$.HCl.¼H$_2$O | A | 248-251 |
| 11 a | H | C$_{23}$H$_{30}$N$_2$O.2HCl | C | 288-290 |
| b | o-Br | C$_{23}$H$_{29}$BrN$_2$O.2HCl | D | 270-273 |
| c | m-Br | C$_{23}$H$_{29}$BrN$_2$O.2HCl | D | 282-286 |
| d | p-Br | C$_{23}$H$_{29}$BrN$_2$O.2HCl | D | 275-278 |
| e | I | C$_{23}$H$_{29}$IN$_2$O.2HCl | D | 230 (sinters) |
| 12 a | H | C$_{23}$H$_{30}$N$_2$O.2HCl.¼H$_2$O | D | 235-236 |
| b | o-F | C$_{23}$H$_{29}$FN$_2$O.2HCl.½H$_2$O | D | 225-227 |
| c | m-F | C$_{23}$H$_{29}$FN$_2$O.2HCl.½H$_2$O | D | 233-235 |
| d | p-F | C$_{23}$H$_{29}$FN$_2$O.2HCl | D | 236-238 |
| e | o-Br | C$_{23}$H$_{29}$BrN$_2$O.2HCl | D | 232-234 |
| f | m-Br | C$_{23}$H$_{29}$BrN$_2$O.2HCl | D | 220-223 |
| g | p-Br | C$_{23}$H$_{29}$BrN$_2$O.¼H$_2$O | D | *159-161 |
| h | I | C$_{23}$H$_{29}$IN$_2$O.2HCl | D | 236-240 |
| i | CH$_3$ | C$_{24}$H$_{32}$N$_2$O.2HCl.½H$_2$O | D | 233-235 |
| j | CH$_3$ | C$_{24}$H$_{32}$N$_2$O.2HCl.½H$_2$O | D | 220-224 |
| k | CH$_3$ | C$_{24}$H$_{32}$N$_2$O.2HCl.½H$_2$O | D | 218-221 |
| 10 b | o-I | C$_{23}$H$_{27}$IN$_2$O$_2$.HCl | E | 263-264 |
| 10 c | m-I | C$_{23}$H$_{27}$IN$_2$O$_2$.HCl | E | 266-269 |
| 10 d | p-I | C$_{23}$H$_{27}$IN$_2$O$_2$.HCl | E | 248-251 |
| 11 f | — | C$_{22}$H$_{27}$N$_3$O$_3$.¼H$_2$O | F | 230-232 |
| 11 l | — | C$_{22}$H$_{27}$N$_3$O$_3$.HCl | F | 247-250 |

[a]All elemental analyses are within ± 0.4% of theoretical unless otherwise specified.

TABLE 2

Inhibitory potency of azavesamicols[a]

| Compound | R | $IC_{50}C(nM)^c$ |
|---|---|---|
| (dl)-vesamicol[b] | — | 34 ± 6 |
| (dl)-4c[d] | — | 170 ± 20 |
| (−)-4c[d] | — | 36 ± 5 |
| (dl)-9 | — | 1900 ± 600 |
| (+)-10 | — | 34 ± 7 |
| (−)-10 | — | 100 ± 30 |
| 11a | H | 83 ± 7 |
| 11b | o-Br | 55 ± 8 |
| 12a | H | 30 ± 7 |
| 12d | p-F | 14 ± 3 |
| 12e | o-Br | 22 ± 6 |
| 12f | m-Br | 21 ± 8 |
| 12g | p-Br | 25 ± 10 |
| 12h | m-I | 26 ± 11 |

[a]The hydrochlorides were tested using highly purified synaptic vesicles harvested from the electric organ of Torpedo Californica.
[b]Data obtained from Bahr and Parsons (1986).
[c]Values are for the inhibition of [$^3$H]vesamicol binding. $IC_{50}$ values are quoted ± 1 standard deviation.
[d]Obtained from Efange et al. (1991)

TABLE 3

Pharmacological Activity of Azavesamicols in mice[a]

| Compound | 1.3 | 2.5 | 5.0 | 10 | 15 | 20 | 30 | 40 | 60 |
|---|---|---|---|---|---|---|---|---|---|
| 5 | | | | | | | | | NR[b] |
| 6 | | | | | | | | | NR |
| 9 | | | | | | | | | LD |
| (dl)-10a | | | | | | LD | | LD | |
| (+)-10a | | + | LD | | | | | LD | |
| (−)-10a | | | + | | | | | | |
| 10[b] | | | NR | | | | + | | |
| 11a | | | | | NR | | + | | |
| 11[b] | | | NR | + | | | | | |
| 11c | | | | | NR | | NR | | NR[c] |
| 11d | | | | | NR | | | | |
| 11f | | | | | | | | | |
| 12a | | | | LD | | | | | |
| 12d | | | | LD | | | | | |
| 12e | | | | LD | | | | | |
| 12f | | | NR | LD | | | | | |
| 12g | | | | | | + | | LD | |
| 12I | | | | | | NR | | | |
| 12h | NR | | LD | | | | | | |

[a]Group of mice (n = 2) received selected doses of the compounds by ip injection. The animals were observed for signs of anticholinergic activity: spasms, respiratory distress, paralysis. At lethal doses, death generally occurred within 10 min following the injection. LD, lethal dose; NR, no visible pharmacological reaction; +, visible anticholinergic effects; S, sluggishness and reduced locomotor activity.
[b]No observable reaction even at 80 umol/Kg.
[c]Hind legs remained visibly paralyzed for at least 15 min post-injection.

TABLE 4

Tissue distribution of (+)-[$^{125}$I]12h in the rat*

% dose/g of tissue (range)

| TISSUE | 5 MIN. (n = 3) | 30 MIN. (n = 3) | 60 MIN. (n = 3) | 180 MIN. (n = 3) |
|---|---|---|---|---|
| blood | 0.24 (0.23–0.26) | 0.12 (0.10–0.13) | 0.09 (0.08–0.10) | 0.07 (0.05–0.07) |
| liver | 1.60 (1.30–1.80) | 2.18 (2.03–2.28) | 1.91 (1.63–2.07) | 1.18 (1.12–1.24) |
| lung | 3.67 (2.96–4.26) | 1.21 (1.06–1.34) | 0.82 (0.60–1.15) | 0.39 (0.35–0.42) |
| kidney | 2.25 (2.00–2.52) | 1.32 (1.14–1.41) | 0.87 (0.78–1.01) | 0.50 (0.45–0.52) |
| muscle | 0.34 (0.24–0.46) | 0.16 (0.15–0.18) | 0.11 (0.10–0.13) | 0.08 (0.06–0.11) |
| spleen | 0.76 (0.54–1.01) | 1.07 (0.87–1.23) | 0.86 (0.73–0.96) | 0.44 (0.42–0.47) |
| heart | 1.14 (0.97–1.26) | 0.26 (0.24–0.29) | 0.15 (0.09–0.19) | 0.10 (0.09–0.11) |
| brain | 0.57 (0.50–0.67) | 0.36 (0.34–0.38) | 0.27 (0.22–0.32) | 0.15 (0.14–0.16) |
| gonads | 0.13 (0.12–0.15) | 0.15 (0.13–0.16) | 0.17 (0.15–0.19) | 0.16 (0.16–0.17) |
| thyroid | 1.60 (1.26–1.89) | 2.33 (1.87–3.09) | 4.59 (3.65–5.81) | 13.13 (11.81–15.60) |
| Ratios | | | | |
| brain/blood | 2.33 (2.16–2.67) | 3.18 (2.77–3.61) | 3.08 (2.62–3.47) | 2.35 (2.06–2.83) |
| heart/blood | 4.68 (4.24–5.01) | 2.33 (2.04–2.54) | 1.70 (0.98–2.21) | 1.60 (1.34–2.04) |

*NOTE: The animals were injected intravenously with 4.9 uCi of the radiotracer in 0.1 ml of 50% aq. EtOH.

TABLE 5

Tissue distribution of (−)-[$^{125}$I]12h in the rat*

| TISSUE | % dose/g of tissue (range) | | | |
|---|---|---|---|---|
| | 5 MIN. (n = 3) | 30 MIN. (n = 3) | 60 MIN. (n = 3) | 180 MIN. (n = 3) |
| blood | 0.22 (0.19–0.25) | 0.11 (0.10–0.13) | 0.10 (0.09–0.10) | 0.10 (0.08–0.12) |
| liver | 2.07 (1.81–2.49) | 2.35 (2.14–2.51) | 2.63 (2.28–3.11) | 2.23 (2.07–2.34) |
| lung | 5.90 (4.65–7.87) | 3.21 (2.87–3.55) | 2.41 (1.99–2.89) | 2.01 (1.87–2.43) |
| kidney | 3.71 (3.23–4.07) | 3.53 (3.29–4.10) | 3.13 (2.62–3.52) | 3.27 (3.02–3.66) |
| muscle | 0.46 (0.24–0.69) | 0.30 (0.23–0.37) | 0.28 (0.26–0.29) | 0.27 (0.21–0.37) |
| spleen | 1.04 (0.92–1.10) | 1.24 (1.20–1.30) | 1.17 (1.00–1.37) | 1.28 (1.25–1.31) |
| heart | 1.32 (1.14–1.50) | 0.75 (0.72–0.77) | 0.58 (0.55–0.64) | 0.50 (0.48–0.52) |
| brain | 0.92 (0.83–1.07) | 0.99 (0.91–1.10) | 0.83 (0.74–0.95) | 0.92 (0.86–1.01) |
| gonads | 0.19 (0.18–0.22) | 0.23 (0.16–0.30) | 0.17 (0.16–0.18) | 0.20 (0.19–0.22) |
| thyroid | 2.67 (2.35–2.97) | 3.15 (2.77–3.81) | 5.87 (4.53–7.42) | 11.55 (8.13–14.65) |
| Ratios | | | | |
| brain/blood | 4.27 (3.42–5.44) | 9.06 (8.63–9.38) | 8.51 (7.94–9.60) | 9.87 (7.97–12.82) |
| heart/blood | 6.07 (5.43–6.71) | 6.87 (6.04–7.34) | 5.97 (5.40–6.48) | 5.32 (4.75–6.37) |

*NOTE: The animals were injected with 3.7 uCi of the radiotracer in 0.1 ml of 50% aq. EtOH.

TABLE 6

Blocking Studies with (−)-[$^{125}$I]11h

| TISSUE | % dose/g of tissue (range) | |
|---|---|---|
| | Group 1 (n = 3) | Group 2 (n = 3) |
| blood | 0.09 (0.09–0.10) | 0.09 (0.08–0.10) |
| liver | 2.45 (2.20–2.88) | 2.31 (2.19–2.40) |
| lung | 1.96 (1.71–2.23) | 0.76 (0.57–0.88) |
| kidney | 3.11 (2.68–3.68) | 0.89 (0.76–0.93) |
| muscle | 0.26 (0.23–0.32) | 0.12 (0.09–0.17) |
| spleen | 1.10 (0.97–1.21) | 0.58 (0.53–0.61) |
| heart | 0.50 (0.46–0.54) | 0.16 (0.14–0.17) |
| brain | 0.97 (0.90–1.06) | 0.29 (0.25–0.31) |
| gonads | 0.21 (0.19–0.22) | 0.22 (0.21–0.24) |
| thyroid | 5.58 (3.69–7.16) | 6.55 (5.85–7.38) |
| Ratios | | |
| brain/blood | 10.44 (9.00–11.78) | 3.30 (2.50–3.75) |
| heart/blood | 5.37 (5.00–6.00) | 1.87 (1.40–2.00) |

*NOTE: Animals in Group 1 received a single i.v. injection of radiotracer. Animals in Group 2 were administered with a mixture of the radiotracer and (dl)-vesamicol hydrochloride (1.05 umol/Kg). All animals were sacrificed at 60 min post-radiotracer injection.

TABLE 7

Effect of vesamicol pretreatment on the accumulation of (−)-[$^{125}$I]12h in the rat

| TISSUE | % dose/g of tissue (range) | |
|---|---|---|
| | Group 1 (n = 3) | Group 2 (n = 3) |
| blood | 0.11 (0.10–0.11) | 0.12 (0.09–0.16) |
| liver | 1.91 (1.63–2.13) | 1.89 (1.52–2.21) |
| lung | 2.36 (2.03–2.73) | 1.59 (1.02–2.18) |
| kidney | 2.45 (1.78–2.73) | 1.13 (0.87–1.35) |
| muscle | 0.18 (0.12–0.25) | 0.16 (0.12–0.20) |
| spleen | 1.05 | 0.80 |

TABLE 7-continued

Effect of vesamicol pretreatment on the accumulation of $(-)$-$[^{125}I]$12hin the rat

| TISSUE | % dose/g of tissue (range) | |
|---|---|---|
| | Group 1 (n = 3) | Group 2 (n = 3) |
| | (0.92–1.18) | (0.62–0.94) |
| heart | 0.59 | 0.30 |
| | (0.57–0.61) | (0.22–0.35) |
| brain | 0.68 | 0.34 |
| | (0.67–0.69) | (0.27–0.38) |
| gonads | 0.15 | 0.16 |
| | (0.14–0.15) | (0.15–0.17) |
| thyroid | 2.62 | 4.56 |
| | (2.22–3.37) | (3.02–6.14) |
| Ratios | | |
| brain/ blood | 6.45 (6.27–6.70) | 2.75 (2.53–2.88) |
| heart/ blood | 5.59 (5.27–5.81) | 2.40 (2.32–2.56) |

At time = 0, animals in group 1 injected intravenously with vehicle (50%) aq. EtOH; 0.2 ml), while animals in group 2 each received an i.v. injection of (dl)-vesamicol. HCl (1.01 umol/Kg). After 15 min, both groups were injected with the radiotracer, allowed to recover and sacrificed 30 min post-radiotracer injection.

While this invention may be embodied in many different forms, there are shown in the drawings and described in detail herein specific preferred embodiments of the invention. The present disclosure is an exemplification of the principles of the invention and is not intended to limit the invention to the particular embodiments illustrated.

This completes the description of the preferred and alternate embodiments of the invention. Those skilled in the art may recognize other equivalents to the specific embodiment described herein which equivalents are intended to be encompassed by the claims attached hereto.

What is claimed is:

1. A method for photoaffinity labelling of the vesamicol protein, which comprises ex vivo treatment of animal tissues containing cholinergic synaptic vesicles with an effective amount of photoaffinity label of the structural formula:

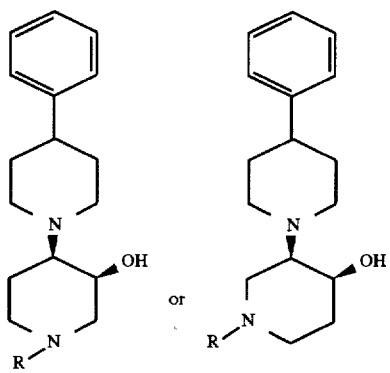

wherein R is:
azidophenyl, azidobenzyl or azidobenzoyl; and inducing chemical bond formation between the azido group and the vesamicol receptor by exposure to light.

2. A method for visualization of cholinergic innervation in the mammalian brain which comprises the application of an effective amount of a composition of the structural formula:

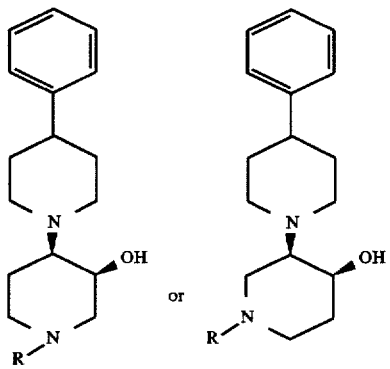

wherein R is azido phenyl, azidobenzyl or azidobenzoyl sidechain containing a fluorescent or visible dye or chromophore; and subsequent visualization of the tissue with light.

* * * * *

UNITED STATES PATENT AND TRADEMARK OFFICE
CERTIFICATE OF CORRECTION

PATENT NO. : 5,789,420
DATED : August 4, 1998
INVENTOR(S) : Simon Mbua, et. al.

It is certified that error appears in the above-identified patent and that said Letters Patent is hereby corrected as shown below:

Title page, item [57], Abstract: delete the entire Abstract and substitute the followings:

A method for non-invasively mapping cholinergic innervation in a living brain comprises injecting the brain with a radiolabelled vesamicol (hydroxylated phencyclidine (PCP) isomer trans-2-(4-phenyl-piperidino)cyclohexanol)derivatives with anticholinergic properties termed herein, "azavesamicols" in which the cyclohexyl group of vesamicol is replaced with a heterocycle of similar size, the piperidyl ring. The radiolabel is then detected externally with a photoscanning device.

Signed and Sealed this

Ninth Day of March, 1999

Attest:

Attesting Officer

Q. TODD DICKINSON

Acting Commissioner of Patents and Trademarks